(12) United States Patent
Zhou et al.

(10) Patent No.: US 10,430,946 B1
(45) Date of Patent: Oct. 1, 2019

(54) MEDICAL IMAGE SEGMENTATION AND SEVERITY GRADING USING NEURAL NETWORK ARCHITECTURES WITH SEMI-SUPERVISED LEARNING TECHNIQUES

(71) Applicant: Inception Institute of Artifical Intelligence, Ltd., Abu Dhabi (AE)

(72) Inventors: Yi Zhou, Abu Dhabi (AE); Xiaodong He, Abu Dhabi (AE); Lei Huang, Abu Dhabi (AE); Li Liu, Abu Dhabi (AE); Fan Zhu, Abu Dhabi (AE); Shanshan Cui, Abu Dhabi (AE); Ling Shao, Abu Dhabi (AE)

(73) Assignee: INCEPTION INSTITUTE OF ARTIFICIAL INTELLIGENCE, LTD., Al Maryah Island (AE)

( * ) Notice: Subject to any disclaimer, the term of this patent is extended or adjusted under 35 U.S.C. 154(b) by 0 days.

(21) Appl. No.: 16/353,800

(22) Filed: Mar. 14, 2019

(51) Int. Cl.
*G06T 7/00* (2017.01)
*G06K 9/62* (2006.01)
*G06T 7/11* (2017.01)
*G06N 3/08* (2006.01)
*G06N 3/04* (2006.01)
(Continued)

(52) U.S. Cl.
CPC .......... *G06T 7/0012* (2013.01); *A61B 5/7267* (2013.01); *G06K 9/628* (2013.01); *G06K 9/6257* (2013.01); *G06K 9/6259* (2013.01); *G06K 9/6263* (2013.01); *G06N 3/04* (2013.01); *G06N 3/088* (2013.01); *G06T 7/11* (2017.01); *G16H 30/40* (2018.01); *G06K 2209/05* (2013.01); *G06T 2207/20081* (2013.01); *G06T 2207/20084* (2013.01); *G06T 2207/30041* (2013.01); *G06T 2207/30096* (2013.01)

(58) Field of Classification Search
CPC ................... G06T 7/0012; G06T 7/11; G06T 2207/20081; G06T 2207/20084; G06T 2207/30096; G06K 9/6257; G06K 9/6263; G06K 9/6259; G06K 9/628; G06K 2209/05; G06K 2207/30041; A61B 5/7267; G16H 30/40; G06N 3/04; G06N 3/088

See application file for complete search history.

(56) References Cited

PUBLICATIONS

Quellec, Gwenolé, et al. "Deep image mining for diabetic retinopathy screening." Medical image analysis 39 (2017): 178-193. (Year: 2017).*

(Continued)

*Primary Examiner* — Menatoallah Youssef
(74) *Attorney, Agent, or Firm* — Bryan Cave Leighton Paisner LLP

(57) ABSTRACT

This disclosure relates to improved techniques for performing computer vision functions on medical images, including object segmentation functions for identifying medical objects in the medical images and grading functions for determining severity labels for medical conditions exhibited in the medical images. The techniques described herein utilize a neural network architecture to perform these and other functions. The neural network architecture can be trained, at least in part, using semi-supervised learning techniques that enable the neural network architecture to accurately perform the object segmentation and grading functions despite limited availability of pixel-level annotation information.

20 Claims, 7 Drawing Sheets
(4 of 7 Drawing Sheet(s) Filed in Color)

(51) Int. Cl.
*G16H 30/40* (2018.01)
*A61B 5/00* (2006.01)

(56) References Cited

PUBLICATIONS

He, Kaiming, et al. "Mask r-cnn." Proceedings of the IEEE international conference on computer vision. 2017. (Year: 2017).*

Hong, Seunghoon, Hyeonwoo Noh, and Bohyung Han. "Decoupled deep neural network for semi-supervised semantic segmentation." Advances in neural information processing systems. 2015. (Year: 2015).*

C. Yu, J. Wang, C. Peng, C. Gao, G. Yu, and N. Sang. Learning a discriminative feature network for semantic segmentation. In CVPR, Jun. 2018.

C. Zhu, X. Tan, F. Zhou, X. Liu, K. Yue, E. Ding, and Y. Ma. Fine-grained video categorization with redundancy reduction attention. In ECCV, Sep. 2018.

Y. Zou, Z. Yu, B. Vijaya Kumar, and J. Wang. Unsupervised domain adaptation for semantic segmentation via class-balanced self-training. In ECCV, Sep. 2018.

Idrid diabetic retinopathy segmentation challenge. https://www.kaggle.com/c/diabetic-retinopathy-detection.

Kaggle diabetic retinopathy detection competition. https://www.kaggle.com/c/diabetic-retinopathy-detection.

International clinical diabetic retinopathy disease seventy scale. American Academy of Ophthalmology, 2012.

P. Anderson, X. He, C. Buehler, D. Teney, M. Johnson, S. Gould, and L. Zhang. Bottom-up and top-down attention for Image captioning and visual question answering. In CVPR, Jun. 2018.

B. Antal, A. Hajdu, et al. An ensemble-based system for microaneurysm detection and diabetic retinopathy grading. IEEE transactions on biomedical engineering, 59(6):1720, 2012.

A. M. Boers, R. S. Barros, I. G. Jansen, C. H. Slump, D. W. Dippel, A van der Lugt, W. H. van Zwam, Y. B. Roos, R. J. van Oostenbrugge, C. B. Majoie, et al. Quantitative collateral grading on ct angiography in patients with acute Ischemic stroke. In MICCAI, pp. 176-184. Springer, 2017.

L. Chen, H. Zhang, J. Xiao, L. Nie, J. Shao, W. Liu, and T.-S. Chua. Sca-cnn: Spatial and channel-wise attention in convolutional networks for image captioning. In CVPR, Jul. 2017.

L.-C. Chen, A. Hermans, G. Papandreou, F. Schroff, P. Wang, and H. Adam. Masklab: Instance segmentation by refining object detection with semantic and direction features. In CVPR, Jun. 2018.

L.-C. Chen, G. Papandreou, I. Kokkinos, K. Murphy, and A. L. Yuille. Deeplab: Semantic image segmentation with deep convolutional nets, atrous convolution, and fully connected crfs. TPAMI, 40(4):834-848, 2018.

X. Chen, J. Hao Liew, W. Xiong, C.-K. Chui, and S. H. Ong. Focus, segment and erase: An efficient network for multi-label brain tumor segmentation. In ECCV, Sep. 2018.

F. Chollet. Xception: Deep learning with depthwise separable convolutions. arXiv preprint, pp. 1610-02357, 2017.

A. V. Dalca, J. Guttag, and M. R. Sabuncu. Anatomical priors in convolutional networks for unsupervised biomedical segmentation. In CVPR, Jun. 2018.

T. de Moor, A. Rodriguez-Ruiz, R. Mann, and J. Teuwen. Automated soft tissue lesion detection and segmentation in digital mammography using a u-net deep learning network. arXiv preprint arXiv:1802.06865, 2018.

E. Decencière, X. Zhang, G. Cazuguel, B. Lay, B. Cochener, C. Trone, P. Gain, R. Ordonez, P. Massin, A. Erginay, et al. Feedback on a publicly distributed image database: the messidor database. Image Analysis & Stereology, 33 (3):231-234, 2014.

D. Doshi, A. Shenoy, D. Sidhpura, and P. Gharpure. Diabetic retinopathy detection using deep convolutional neural networks. In Computing, Analytics and Security Trends (CAST), International Conference on, pp. 261-266. IEEE, 2016.

R. Fan, Q. Hou, M. M. Cheng, G. Yu, R. R. Martin, and S.-M. Hu. Associating inter-image salient instances for weakly supervised semantic segmentation In ECCV, Sep. 2018.

P- Filipczuk, M. Kowal, and A. Marciniak. Feature selection for breast cancer malignancy classification problem. Journal of Medical Informatics & Technologies, 15:193-199, 2010.

I. Goodfellow, J. Pouget-Abadie, M. Mirza, B. Xu, D. Warde-Farley, S. Ozair, A. Courville, and Y. Bengio. Generative adversarial nets. In Advances in NIPS, pp. 2672-2680, 2014.

V. Gulshan, L. Peng, M. Coram, M. C. Stumpe, D. Wu, A. Narayanaswamy, S. Venugopalan, K. Widner, T. Madams, J. Cuadros, et al. Development and validation of a deep learning algorithm for detection of diabetic retinopathy in retinal fundus photographs. Jama, 316(22):2402-2410, 2016.

K. He, G. Gkioxari, P. Dollár, and R. Girshick. Mask r-cnn. In ICCV, pp. 2980-2988. IEEE, 2017.

S. Hong, H. Noh, and B. Han. Decoupled deep neural network for semi-supervised semantic segmentation. In NIPS, pp. 1495-1503, 2015.

W.-C. Hung, Y. H. Tsai, Y.-T. Liou, Y.-Y. Lin, and M.-H. Yang. Adversarial learning for semi-supervised semantic segmentation. arXiv preprint arXiv:1802.07934, 2018.

Q. Li, A. Arnab, and P. H. Torr. Weakly- and semi-supervised panoptic segmentation. In ECCV, Sep. 2018.

T.-Y. Lin, P. Goyal, R. Girshick, K. He, and P. Dollár. Focal loss for dense object detection. TPAMI, 2018.

Z. Lin, R. Guo, Y. Wang, B. Wu, T. Chen, W. Wang, D. Z. Chen, and J. Wu. A framework for identifying diabetic retinopathy based on anti-noise detection and attention-based fusion. In MICCAI, pp. 74-82. Springer, 2018.

J. Long, E. Shelhamer, and T. Darrell. Fully convolutional networks for semantic segmentation. In CVPR, pp. 3431-3440, 2015.

X. Long, C. Gan, G. de Melo, J. Wu, X. Liu, and S. Wen. Attention clusters: Purely attention based local feature Integration for video classification. In CVPR, Jun. 2018.

E. Miranda, M. Aryuni, and E. Irwansyah. A survey of medical image classification techniques. In Information Management and Technology (ICIMTech), International Conference on, pp. 56-61. IEEE, 2016.

T. Nair, D. Precup, D. L. Arnold, and T. Arbel. Exploring uncertainty measures in deep networks for multiple sclerosis lesion detection and segmentation in MICCAI, pp. 655-663. Springer, 2018.

D. Nie, Y. Gao, L. Wang, and D. Shen. Asdnet: Attention based semi-supervised deep networks for medical image segmentation. In MICCAI, pp. 370-378. Springer, 2018.

G. Papandreou, L.-C. Chen, K. P. Murphy, and A. L. Yuille. Weakly- and semi-supervised learning of a deep convolutional network for semantic image segmentation. In ICCV, Dec. 2015.

P. Porwal, S. Pachade, R. Kamble, M. Kokare, G. Deshmukh, V. Sahasrabuddhe, and F. Meriaudeau. Indian diabetic retinopathy image dataset (idrid): A database for diabetic retinopathy screening research. Data, 3(3):25, 2018.

H. Pratt F. Coenen, D. M. Broadbent, S. P. Harding, and Y. Zheng. Convolutional neural networks for diabetic retinopathy. Procedia Computer Science, 90:200-205, 2016.

S. Qiao, W. Shen, Z. Zhang, B. Wang, and A. Yuille. Deep co-training for semi-supervised image recognition. In ECCV, Sep. 2018.

T. Robert, N. Thome, and M. Cord. Hybridnet: Classification and reconstruction cooperation for semi-supervised learning. In ECCV, Sep. 2018.

O. Ronneberger, P. Fischer, and T. Brox. U-net: Convolutional networks for biomedical image segmentation. In MIC-CAI, pp. 234-241. Springer, 2015.

C. I. Sánchez, M. Niemeijer, A. V. Dumitrescu, M. S. Suttorp-Schulten, M. D. Abramoff, and B. van Ginneken. Evaluation of a computer-aided diagnosis system for diabetic retinopathy screening on public data. Investigative ophthalmology & visual science, 52(7):4866-4871, 2011.

N. Sarafianos, X. Xu, and I. A. Kakadiaris. Deep imbalanced attribute classification using visual attention aggregation. In ECCV, Sep. 2018.

(56) References Cited

PUBLICATIONS

F. Sener and A. Yao. Unsupervised learning and segmentation of complex activities from video. In CVPR, Jun. 2018.

L. Seoud, J. Chelbi, and F. Cheriet. Automatic grading of diabetic retinopathy on a public database, In MICCAI. Springer, 2015.

L. Seoud, T. Hurtut, J. Chelbi, F. Cheriet, and J. P. Langlois. Red lesion detection using dynamic shape features for diabetic retinopathy screening. IEEE transactions on medical imaging, 35(4):1116-1126, 2016.

C. Szegedy, V. Vanhoucke, S. Ioffe, J. Shlens, and Z. Wojna. Rethinking the inception architecture for computer vision. In CVPR, pp. 2818-2826, 2016.

M. J. van Grinsven, B. van Ginneken, C. B. Hoyng, T. Theelen, and C. I. Sánchez. Fast convolutional neural network training using selective data sampling: application to hemorrhage detection in color fundus images. IEEE transactions on medical imaging, 35(5):1273-1284, 2016.

H. H. Vo and Verma. New deep neural nets for fine-grained diabetic retinopathy recognition on hybrid color space. In Multimedia (ISM), 2016 IEEE International Symposium on, pp. 209-215. IEEE, 2016.

X. Wang, S. You, X. Li, and H. Ma. Weakly-supervised semantic segmentation by iteratively mining common object features. In CVPR, Jun. 2018.

Z. Wang, Y. Yin, J. Shi, W. Fang, H. Li, and X. Wang. Zoom-in-net: Deep mining lesions for diabetic retinopathy letection. In MICCAI, pp. 267-275. Springer, 2017.

Y. Wei, H. Xiao, H. Shi, Z. Jie, J. Feng, and T. S. Huang. Revisiting dilated convolution: A simple approach for weakly-and semi-supervised semantic segmentation. In CVPR, Jun. 2018.

T. Xu, P. Zhang, Q. Huang, H. Zhang, Z. Gan, X. Huang, and X. He. Attngan: Fine-grained text to image generation with attentional generative adversarial networks. In CVPR, Jun. 2018.

K. Yan, X. Wang, L Lu, and R. M. Summers. Deeplesion: automated mining of large-scale lesion annotations and universal lesion detection with deep learning. Journal of Medical Imaging, 5(3)1):036501, 2018.

Y. Yang, T. Li, W. Li, H. Wu, W. Fan, and W. Zhang. Lesion detection and grading of diabetic retinopathy via two-stages deep convolutional neural networks. In MICCAI, pp. 533-540. Springer, 2017.

\* cited by examiner

US 10,430,946 B1

MEDICAL IMAGE SEGMENTATION AND SEVERITY GRADING USING NEURAL NETWORK ARCHITECTURES WITH SEMI-SUPERVISED LEARNING TECHNIQUES

TECHNICAL FIELD

This disclosure is related to improved techniques for performing computer vision functions and, more particularly, to techniques that utilize trained neural networks and artificial intelligence (AI) algorithms to perform medical object segmentation, disease grading and classification, and other computer vision functions.

BACKGROUND

Performing automated diagnosis functions by analyzing medical images using computer vision applications is a very complex and challenging task. To accurately perform automated diagnosis functions, the computer vision applications must account for a variety of technical problems. One such technical problem relates to training a model that can accurately perform object segmentation on the images to detect medical objects (e.g., lesions or cancerous cells) of interest with pixel-level accuracy. In many cases, this can be difficult because the medical objects often are very small and can have large intra-class variations, which results in the model failing to identify some or all of the objects in the images. Another technical problem relates to training a model that can accurately predict classification labels associated with diagnosing a disease or medical condition. The accuracy of the predictions can be negatively affected if the medical objects are not accurately identified and/or the model is unable to distinguish between similar, but different, medical objects (e.g., different types of lesion conditions or cancer conditions).

Another technical problem relates to providing an appropriate training procedure that can be used to train the object segmentation and disease grading models. Although it may be preferable in many cases to employ a fully-supervised learning approach in which all training data is fully annotated, it is not practical to do so because the available training data is often very limited and the process of annotating medical images is expensive given that it typically requires the very time-consuming dedication of medical domain experts. This is especially true for pixel-level annotations that identify the medical objects of interest. On the other hand, utilizing a purely unsupervised learning approach can also be unacceptable in many cases due to the limited accuracy of the models that can be generated using such approaches.

BRIEF DESCRIPTION OF DRAWINGS

The patent or application file contains at least one drawing executed in color. Copies of this patent or patent application publication with color drawing(s) will be provided by the Office, upon request and payment of the necessary fee.

To facilitate further description of the embodiments, the following drawings are provided, in which like references are intended to refer to like or corresponding parts, and in which.

DETAILED DESCRIPTION OF EXEMPLARY EMBODIMENTS

Figure 1:
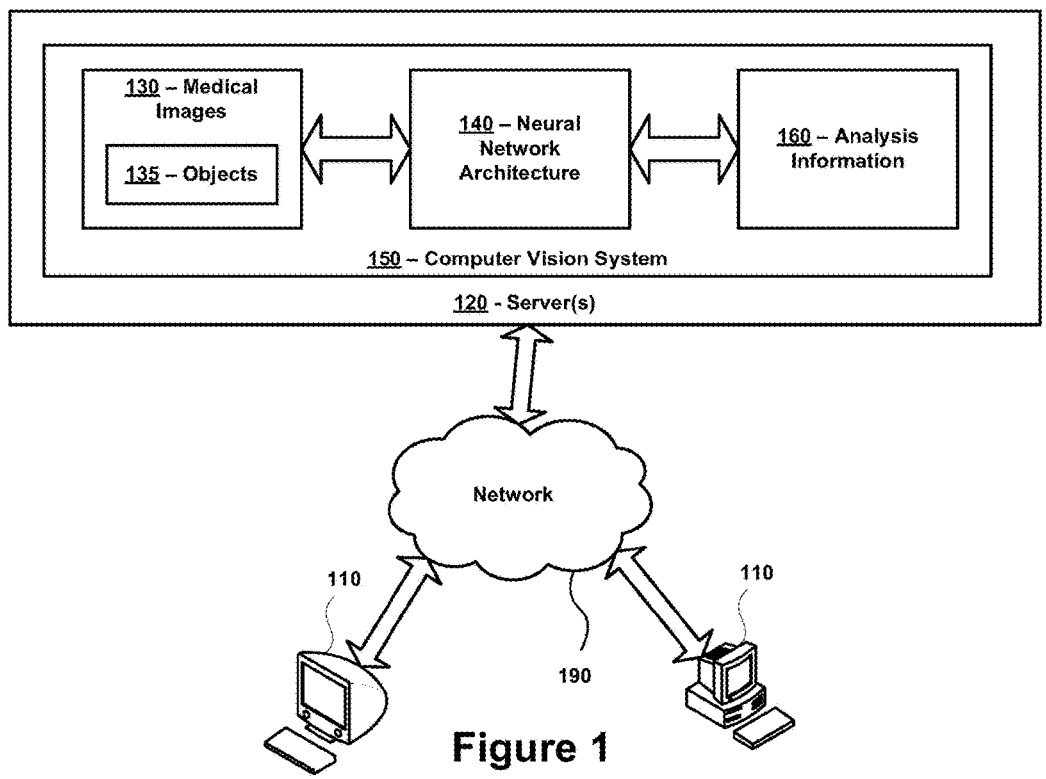
FIG. 1 is a diagram of an exemplary system in accordance with certain embodiments.

The present disclosure relates to systems, methods and apparatuses that utilize improved techniques for performing computer vision functions associated with automated diagnosis functions. A computer vision system includes a neural network architecture that can be trained to perform automated diagnosis functions for a variety of medical conditions. In certain embodiments, the computer vision system can be configured to perform the automated diagnoses functions in connection with diabetic retinopathy (DR). This can include analyzing medical images, such as eye fundus images or other eye-related images, to identify lesion objects and to determine severity ratings for the medical images based, at least in part, on the identified lesion objects. The computer vision system can additionally, or alternatively, be configured to perform the automated diagnoses functions for other medical conditions. For example, the computer vision system can be trained using the techniques disclosed herein to analyze other types of medical images, such as images generated from computerized tomography (CT or CAT) scans, x-ray scans, magnetic resonance imaging (MRI) scans, and/or positron-emission tomography (PET) scans, in order to detect various types of medical objects (e.g., objects related to cancer-related conditions, bone abnormalities, nerve abnormalities, heart abnormalities, etc.) and to determine a severity grading of a disease based on the characteristics of the detected objects.

In certain embodiments, the computer vision system comprises a neural network architecture that includes a segmentation model and a grading model. The segmentation model can be trained to perform object segmentation functions on the medical images in order to detect various types of medical-related objects (e.g., such as lesions, tumors, cancerous cells, etc.) with pixel-level accuracy. The grading model can be trained to predict a classification labels that indicate the severity of medical conditions pertaining to the medical images. For embodiments in which the computer vision system is trained to perform automated disease diagnoses functions for diabetic retinopathy, the segmentation model can be trained to identify lesions included in the medical images (e.g., which can include fundus images and/or other eye-related images); and the grading model can be configured to assign labels to the medical images indicating the severity of the diabetic retinopathy condition (e.g., indicating whether a detected diabetic retinopathy condition has progressed to a normal stage, mild stage, moderate stage, severe non-proliferative stage and/or proliferative stage). For embodiments in which the computer vision system is trained to perform automated disease diagnoses functions for other types of medical conditions, the segmentation model can be trained to identify appropriate medical objects of interest (e.g., objects associated with cancer, bone abnormalities, nerve abnormalities, heart abnormalities, etc.); and the grading model can be configured to assign appropriate labels to the medical images indicating the severity of the medical condition.

The procedures that are utilized to train the neural network architecture of the computer vision system can vary. In certain embodiments, the neural network architecture is trained, at least in part, using a semi-supervised training procedure, which greatly reduces the need for pixel-level annotations that are typically used for learning object segmentation functions (e.g., which, in many cases, can require point-level annotations or bounding boxes to be utilized to identify medical objects during training). While large quantities of training images with pixel-level annotations may be obtained for certain types of general object segmentation tasks, such information is typically unavailable in the context of medical images. This can be attributed, at least in part, to the fact that assigning pixel-wise annotations to medical images is very time-consuming and can require medical domain experts to expend great efforts to manually annotate the images. As a result, the time and expense required to generate a sufficient number of training images that include pixel-level annotations is often impossible or impractical. The semi-supervised training procedure described herein enables the segmentation and grading models to learn functions for accurately performing object segmentation and disease grading, despite the fact that there is only a limited number of training images with pixel-level annotations.

The training procedure can employ a collaborative learning approach that jointly optimizes the performance of the segmentation and grading models. As mentioned above, the semi-supervised training procedure may utilize a set of training images that have limited annotations to train the models. For example, a first subset of the training images may include a relatively small number of images that include pixel-level annotations (e.g., pixel-level annotations that identify lesions and/or other medical objects of interest with pixel-level accuracy), and a second subset of the training images include a relatively large number of training images that only include image-level annotations (e.g., that identify the severity classification labels for the images) and do not include pixel-level annotations.

In a first training step, the segmentation model can be pre-trained using the first subset of the training images which include the pixel-level annotations (e.g., ground-truth masks), and the grading model can be pre-trained using the second subset of the training images that include the image-level annotations. Both models can be trained in a fully-supervised manner during this pre-training step. Once the pre-training is complete, the segmentation model can process the second subset of training images in order to generate weak, predicted masks that identify medical objects of interest included in the second subset of training images. The weak, predicted masks can then be utilized to improve the performance of the grading model with respect to predicted severity classification labels. These weak, predicted masks can further be utilized by the pre-trained grading model to generate pseudo masks based on the second subset of the training images. In turn, the pseudo masks generated by the grading model can be used to optimize the segmentation model using a semi-supervised training approach. As part of this semi-supervised training approach, a generative adversarial network (GAN) can receive the weakly predicted masks as real samples and the pseudo masks as fake samples while trying to distinguish between each other. The feedback from the can then be utilized to optimize the segmentation model. In this manner, the performance of the segmentation and grading models can be jointly optimized.

Extensive ablation studies and comparative experiments were conducted which demonstrate the effectiveness of the aforementioned collaborative training techniques. Amongst other things, it has been shown that image-level annotations included in the large-scale second subset of the training images can be used to significantly improve the accuracy of the segmentation model with respect to identify medical objects, while the limited pixel-level annotations included in the first subset of the training images can significantly improve the grading performance of the grading model with respect to predicting severity classification labels.

The technologies discussed herein can be used in a variety of different contexts and environments. One useful application of these technologies is in the context of medical systems and/or applications. For example, integrating these technologies into a medical system or application would permit a doctor, technician, researcher, or other individual to quickly identify medical objects (e.g., lesions or cancerous cells) of interest and to determine a severity of any corresponding medical condition. For example, in the context of diabetic retinopathy, these technologies can be used to detect lesions in fundus images or other eye-related images and to determine a severity of a diabetic retinopathy condition in each of the images. Similarly, in the context of cancer detection, these technologies can be used to detect cancerous objects (e.g., cancer cells, tumors, etc.) in medical images (e.g., corresponding to mammography scans or other types of cancer-screening scans) and to determine the severity of a cancer-related condition in each of the images. Another useful application of these technologies is in the context of computer vision, which can be applied across a wide variety of different applications. For example, the technologies disclosed herein may be integrated into any application, device, or system that can benefit from object segmentation and/or classification. The technologies discussed herein can be applied to many other contexts as well.

As evidenced by the disclosure herein, the inventive techniques set forth in this disclosure are rooted in computer technologies that overcome existing problems in known computer vision systems; specifically problems dealing with object segmentation, classification, and automated diagnosis functions. The techniques described in this disclosure provide a technical solution (e.g., one that utilizes various AI-based neural networking and machine learning techniques) for overcoming the limitations associated with known techniques. For example, the image analysis techniques described herein take advantage of novel AI and machine learning techniques to learn functions for automating medical object segmentation, classification, and diagnosis functions. Moreover, in certain embodiments, these functions can be learned using semi-supervised training techniques that reduce the need for instance-level supervision, which typically requires user-intensive annotations on the images and corresponding objects. This technology-based solution marks an improvement over existing capabilities and functionalities related to computer vision systems by improving the accuracy of the computer vision functions and reducing the information that is required to train the neural network architectures to perform such functions.

In certain embodiments, a computer vision system is provided for analyzing medical images. The system includes one or more computing devices comprising one or more processors and one or more non-transitory storage devices for storing instructions, wherein execution of the instructions by the one or more processors causes the one or more computing devices to: receive a set of training images including a first subset of training images comprising pixel-level annotation information and a second subset of training images comprising image-level annotation information; execute a training procedure that jointly trains a segmentation model to identify medical objects included in medical images and a grading model to assign severity classification labels to the medical images, wherein executing the training procedure includes: (i) executing a pre-training procedure that uses a fully-supervised training approach to train the segmentation model with the first subset of training images and the grading model with the second subset of training images; (ii) generating, using the segmentation model, predicted masks based on the second subset of training images after the pre-training procedure is performed; (iii) utilizing the predicted masks to train an attention function of the grading model; (iv) generating, using the attention function of the grading model, pseudo masks based on the second subset of training images; and (v) utilizing the predicted masks and the pseudo masks to further train the segmentation model using a semi-supervised training approach; receive a medical image; and generate, using the segmentation model and the grading model, analysis information for the medical image that identifies a severity classification label for the medical image and one or more medical objects included in the medical image.

In certain embodiments, a method is provided for providing a computer vision system. The method comprises: receiving a set of training images including a first subset of training images comprising pixel-level annotation information and a second subset of training images comprising image-level annotation information; executing a training procedure that jointly trains a segmentation model to identify medical objects included in medical images and a grading model to assign severity classification labels to the medical images, wherein executing the training procedure includes: (i) executing a pre-training procedure that uses a fully-supervised training approach to train the segmentation model with the first subset of training images and the grading model with the second subset of training images; (ii) generating, using the segmentation model, predicted masks based on the second subset of training images after the pre-training procedure is performed; (iii) utilizing the predicted masks to train an attention function of the grading model; (iv) generating, using the attention function of the grading model, pseudo masks based on the second subset of training images; and (v) utilizing the predicted masks and the pseudo masks to further train the segmentation model using a semi-supervised training approach; receiving a medical image; and generating, using the segmentation model and the grading model, analysis information for the medical image that identifies a severity classification label for the medical image and one or more medical objects included in the medical image.

In certain embodiments, a computer program product is provided. The computer program product comprises a non-transitory computer-readable medium including instructions for causing a computer to: receive a set of training images including a first subset of training images comprising pixel-level annotation information and a second subset of training images comprising image-level annotation information; execute a training procedure that jointly trains a segmentation model to identify medical objects included in medical images and a grading model to assign severity classification labels to the medical images, wherein executing the training procedure includes: (i) executing a pre-training procedure that uses a fully-supervised training approach to train the segmentation model with the first subset of training images and the grading model with the second subset of training images; (ii) generating, using the segmentation model, predicted masks based on the second subset of training images after the pre-training procedure is performed; (iii) utilizing the predicted masks to train an attention function of the grading model; (iv) generating, using the attention function of the grading model, pseudo masks based on the second subset of training images; and (v) utilizing the predicted masks and the pseudo masks to further train the segmentation model using a semi-supervised training approach; receive a medical image; and generate, using the segmentation model and the grading model, analysis information for the medical image that identifies a severity classification label for the medical image and one or more medical objects included in the medical image.

The embodiments described in this disclosure can be combined in various ways. Any aspect or feature that is described for one embodiment can be incorporated to any other embodiment mentioned in this disclosure. Moreover, any of the embodiments described herein may be hardware-based, may be software-based or may comprise a mixture of both hardware and software elements. Thus, while the description herein may describe certain embodiments, features, or components as being implemented in software or hardware, it should be recognized that any embodiment, feature or component that is described in the present application may be implemented in hardware and/or software.

Embodiments may include a computer program product accessible from a computer-usable or computer-readable medium providing program code for use by or in connection with a computer or any instruction execution system. A computer-usable or computer-readable medium may include any apparatus that stores, communicates, propagates, or transports the program for use by or in connection with the instruction execution system, apparatus, or device. The medium can be a magnetic, optical, electronic, electromagnetic, infrared, or semiconductor system (or apparatus or device), or may be a propagation medium. The medium may include a computer-readable storage medium, such as a semiconductor, solid state memory, magnetic tape, a removable computer diskette, a random access memory (RAM), a read-only memory (ROM), a programmable read only memory (PROM), a static random access memory (SRAM), a rigid magnetic disk and/or an optical disk, etc.

A data processing system suitable for storing and/or executing program code may include at least one processor coupled directly or indirectly to memory elements through a system bus. The at least one processor can include: one or more central processing units (CPUs), one or more graphical processing units (CPUs), one or more controllers, one or more microprocessors, one or more digital signal processors, and/or one or more computational circuits. The memory elements can include local memory employed during actual execution of the program code, bulk storage and cache memories that provide temporary storage of at least some program code to reduce the number of times code is retrieved from bulk storage during execution. Input/output or I/O devices (including but not limited to keyboards, displays, pointing devices, etc.) may be coupled to the system, either directly or through intervening I/O controllers.

Network adapters may also be coupled to the system to enable the data processing system to become coupled to other data processing systems, remote printers, or storage devices through intervening private or public networks. Modems, cable modems and Ethernet cards are just a few of the currently available types of network adapters.

FIG. 1 is a diagram of an exemplary system 100 in accordance with certain embodiments. The system 100 comprises one or more computing devices 110 and one or more servers 120 that are in communication over a network 190. A computer vision system 150 is stored on, and executed by, the one or more servers 120. The network 190 may represent any type of communication network, e.g., such as one that comprises a local area network (e.g., a Wi-Fi network), a personal area network (e.g., a Bluetooth network), a wide area network, an intranet, the Internet, a cellular network, a television network, and/or other types of networks.

All the components illustrated in FIG. 1, including the computing devices 110, servers 120, and computer vision system 150, can be configured to communicate directly with each other and/or over the network 190 via wired or wireless communication links, or a combination of the two. Each of the computing devices 110, servers 120 and computer vision system 150 can also be equipped with one or more transceiver devices, one or more computer storage devices (e.g., RAM, ROM, PROM, SRAM, etc.), and one or more processing devices (e.g., CPUs, GPUs, etc.) that are capable of executing computer program instructions. The computer storage devices can be physical, non-transitory mediums.

In certain embodiments, the computing devices 110 may represent desktop computers, laptop computers, mobile devices (e.g., smart phones, personal digital assistants, tablet devices, vehicular computing devices, or any other device that is mobile in nature), and/or other types of devices. The one or more servers 120 may generally represent any type of computing device, including any of the computing devices 110 mentioned above. In certain embodiments, the one or more servers 120 comprise one or more mainframe computing devices that execute web servers for communicating with the computing devices 110 and other devices over the network 190 (e.g., over the Internet).

In certain embodiments, the computer vision system 150 is stored on, and executed by, the one or more servers 120. The computer vision system 150 can be configured to perform any and all functions associated with analyzing medical images 130 and/or generating analysis information 160. This may include, but is not limited to, computer vision functions related to performing object segmentation (e.g., which may include identifying locations of objects 135 in the medical images 130), object classification (e.g., which may include classifying the objects identified in the medical images 130), and/or medical condition grading (e.g., which may include predicting classification labels that indicate a severity of one or more medical conditions in each of the medical images 130).

The medical images 130 provided to, and analyzed by, the computer vision system 150 can include any type of image. In certain embodiments, the medical images 130 can include one or more two-dimensional (2D) images. In certain embodiments, the medical images 130 may include one or more three-dimensional (3D) images. The medical images 130 may be captured in any digital or analog format and may be captured using any color space or color model. Exemplary image formats can include, but are not limited to: JPEG (Joint Photographic Experts Group), TIFF (Tagged Image File Format), GIF (Graphics Interchange Format), PNG (Portable Network Graphics), etc. Exemplary color spaces or models can include, but are not limited to sRGB (standard Red-Green-Blue), Adobe RGB, gray-scale, etc. In certain embodiments, pre-processing functions can be applied to the medical images 130 to adapt the medical images 130 to format that can assist the computer vision system 150 with analyzing the medical images 130.

The medical images 130 can generally include any image that is useful for analyzing and/or diagnosing a medical condition. Generally speaking, the computer vision system 150 can be adapted to assist with diagnosing any type of medical condition including, but not limited to, eye-related conditions, cancer-related conditions, bone-related conditions, nerve-related conditions, heart-related conditions, organ-related conditions, blood-related conditions, brain-related conditions, etc. The types of medical images 130 provided to the computer vision system can vary based on the types of medical conditions the computer vision system 150 is trained to assess. As explained in further detail below, in certain embodiments, the medical images 130 may correspond to eye-related images, and the computer vision system 150 can be configured to analyze the eye-related images to detect various eye-related medical conditions (e.g., diabetic retinopathy or other eye-related conditions).

The images 130 received by the computer vision system 150 can be captured by any type of image capturing device. Such devices can include imaging sensors, cameras, scanning devices and/or optical devices. For example, the image capturing devices can include fundus cameras, slit lamp cameras, ophthalmic imaging devices, CT or CAT scanning devices, x-ray scanning devices, MRI scanning devices, PET scanning devices and/or other types of scanning devices. The image capturing devices can further include still image cameras, video cameras and/or other devices that include image/video sensors. In certain embodiments, the image capturing devices can be equipped with analog-to-digital (ND) converters and/or digital-to-analog (D/A) converters based on the configuration or design of the image capturing devices.

Some or all of the medical images 130 can include one or more objects 135. Generally speaking, any type of object may be included in a medical image 130, and the types of objects 135 included in a medical image 130 can vary greatly based on medical conditions which are being analyzed by the computer vision system 150. In certain embodiments, the objects 135 included in a medical image 130 can correspond to any content in the medical images 130 that is associated with a medical condition and/or that can be useful for analyzing or diagnosing a medical condition.

For example, for embodiments in which the computer vision system 150 is trained to provide assistance with assessing diabetic retinopathy symptoms, a medical image 130 can include objects 135 corresponding to various types of lesions (e.g., such as aneurysms, micro-aneurysms, hemorrhages, hard exudates, soft exudates and/or other types of lesions) that are present on an image of eye, and/or any other eye-related objects (e.g., blood vessels, optic nerves, etc.) that can assist with analyzing the diabetic retinopathy symptoms. Likewise, for embodiments in which the computer vision system 150 is trained to provide assistance with assessing cancer-related symptoms, a medical image 130 can include objects 135 corresponding to cancer-related conditions (e.g., cancerous cells, tumors, etc.) and/or other objects that can assist with analyzing the cancer-related symptoms. For other types of medical conditions, the objects 135 can correspond to bone abnormalities, nerve abnormalities, heart abnormalities, organ abnormalities, brain abnormalities, etc.

The medical images 130 received by the computer vision system 150 can be provided to the neural network architecture 140 for processing and/or analysis. In certain embodiments, the neural network architecture 140 may comprise a convolutional neural network (CNN), or a plurality of convolutional neural networks. Each CNN may represent an artificial neural network that is inspired by biological processes, and may be configured to analyze medical images 130, and to execute deep learning functions and/or machine learning functions on the medical images 130. Each CNN may include a plurality of layers including, but not limited to, one or more input layers, one or more output layers, one or more convolutional layers (e.g., that include learnable filters), one or more ReLU (rectifier linear unit) layers, one or more pooling layers, one or more fully connected layers, one or more normalization layers, etc. The configuration of the CNNs and their corresponding layers enable the CNNs to learn and execute various functions for analyzing, interpreting and understanding the medical images 130. Exemplary configurations of the neural network architecture 140 are discussed in further detail below.

In certain embodiments, the neural network architecture 140 can be trained to perform one or more computer vision functions to analyze the medical images 130. For example, the neural network architecture 140 can analyze a medical image 130 to perform object segmentation functions, which may include identifying locations of the objects 135 in the medical image 130. In certain embodiments, the object segmentation functions can identify the locations of objects 135 with pixel-level accuracy. The neural network architecture 140 can additionally analyze the medical images 130 to perform grading functions, which may include rating the severity of diseases and/or other medical conditions. For example, the grading functions performed by the neural network architecture 140 can be configured to predict the classification label indicating a severity of a disease or medical condition.

In certain embodiments, the medical images 130 may correspond to eye-related images and the neural network architecture 140 can be configured to analyze the eye-related images to detect various eye-related medical conditions. For example, the medical images 130 may represent fundus images that are captured with fundus cameras, and/or other images of eyes that are captured with optical and/or ophthalmic devices. In such embodiments, one or more of the medical images 130 may include objects 135 that are indicative of eye-related medical conditions or diseases. For example, in certain embodiments, the objects 135 may correspond to lesion symptoms, such as micro-aneurysms, hemorrhages, hard exudates, soft exudates and/or other related objects that are associated with diabetic retinopathy symptoms. The neural network architecture 140 can be trained to perform object segmentation functions on the medical images 130 to identify the locations the objects 135 in the medical images 130. The neural network architecture 140 can be further trained to determine the severity of the diabetic retinopathy condition in each of the medical images 130. In certain embodiments, the severity of the diabetic retinopathy condition can be graded into one of five stages: normal, mild, moderate, severe non-proliferative and proliferative according to certain medical protocols. The neural network architecture 140 can be trained to determine and/or predict a classification label indicating the severity stage of each medical image 130. In the event that a medical image 130 does not include any objects 135 corresponding to a diabetic retinopathy condition, the neural network architecture 140 may output a label or other indicator indicating that the non-existence of a diabetic retinopathy condition.

The medical images 130 analyzed by the neural network architecture 140 can alternatively, or additionally, include other types of medical images 130. For example, in certain embodiments, the medical images 130 can include images that are generated from CT or CAT scans, x-ray scans, MRI scans, PET scans and/or other types of scans. The neural network architecture 140 can be configured to analyze these images to detect various types of objects 135 that are associated one or more medical conditions. For example, the neural network architecture 140 can analyze the medical images to detect one or more objects 135 associated with cancer-related medical conditions or other medical conditions that are capable of being detected by such scans. The neural network architecture 140 can further determine a severity grading of a disease or medical condition based on the characteristics of the detected objects 135.

The neural network architecture 140 of the computer vision system 150 can be configured to generate and output analysis information 160 based on an analysis of the medical images 130. The analysis information 160 for an image 130 can generally include any information or data associated with analyzing, interpreting, understanding and/or classifying the medical images 130 or the objects 135 included in the medical images 130. In certain embodiments, the analysis information 160 can include information or data that indicates the results of the computer vision functions performed by the neural network architecture 140. For example, the analysis information 160 may include information that identifies the results associated with performing the object segmentation functions, grading functions and/or other functions.

In certain embodiments, the analysis information 160 can include information that indicates whether or not one or more medical conditions were detected in each of the medical images 160. The analysis information 160 can further include a severity indication that identifies the severity of each detected medical condition. The analysis information 160 can further include data that indicates the locations of the objects 135 identified in each of the medical images 130. For example, the analysis information 160 for an image 130 can include an annotated version of a medical image 130 which identifies each of the objects 135 (e.g., lesions, cancel-related objects, etc.) included in the image, and which includes lines or annotations surrounding the perimeters, edges, or boundaries of the objects 135. The analysis information 160 can include other types of data or information for identifying the locations of the objects (e.g., such as coordinates of the objects 135 and/or masks identifying locations of objects 135). Other types of analysis information 160 can be output by the neural network architecture 140 as well.

As discussed in further detail throughout this disclosure, the neural network architecture 140 can be trained to perform these and other computer vision functions using a semi-supervised training procedure. The semi-supervised training procedure trains the neural network architecture 140 to accurately identify objects 135 with great intra-class variance and to accurately rate the severity of medical conditions, despite being trained with limited annotation information for a training set of images.

In the exemplary system 100 shown in FIG. 1, the computer vision system 150 may be stored on, and executed by, the one or more servers 120. In other exemplary systems, the computer vision system 150 can additionally, or alternatively, be stored on, and executed by, the computing devices 110 and/or other devices. For example, in certain embodiments, the computer vision system 150 can be integrated directly into an image capturing device that captures a medical image 130 to enable the camera device 130 to analyze the medical image 130 using the techniques described herein. Likewise, the computer vision system 150 can also be stored as a local application on a computing device 110, or integrated with a local application stored on a computing device 110 to implement the techniques described herein. For example, in certain embodiments, the computer vision system 150 can be integrated with (or can communicate with) various applications including, but not limited to, medical applications, research applications and/or other applications that are stored on a computing device 110 and/or server 120.

In certain embodiments, the one or more computing devices 110 can enable individuals to access the computer vision system 150 over the network 190 (e.g., over the Internet via a web browser application). For example, after an image capturing device has captured one or more images 130, an individual can utilize the image capturing device or a computing device 110 to transmit the one or more images 130 over the network 190 to the computer vision system 150. The computer vision system 150 can analyze the one or more images 130 using the techniques described in this disclosure. The analysis information 160 generated by the computer vision system 150 can be transmitted over the network 190 to the image capturing device and/or computing device 110 that transmitted the one or more images 130.

Figure 2:
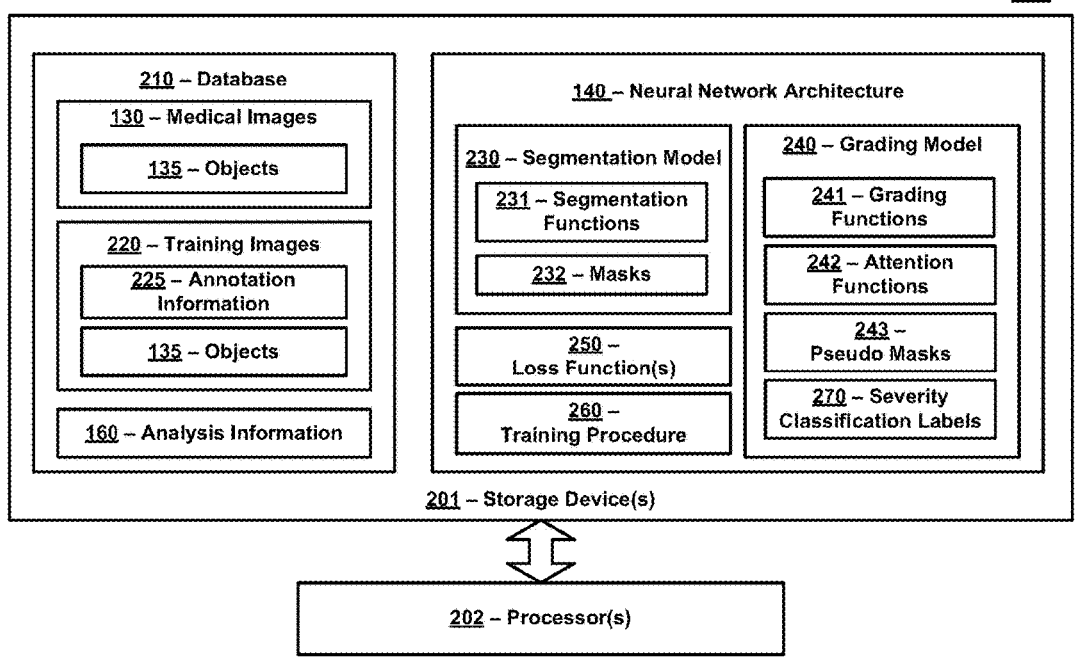
FIG. 2 is a block diagram of an exemplary computer vision system in accordance with certain embodiments.

FIG. 2 is a block diagram of a computer vision system 150 in accordance with certain embodiments. The computer vision system 150 includes one or more storage devices 201 that are in communication with one or more processors 202. The one or more storage devices 201 can include: i) non-volatile memory, such as, for example, read only memory (ROM) or programmable read only memory (PROM); and/or (ii) volatile memory, such as, for example, random access memory (RAM), dynamic RAM (DRAM), static RAM (SRAM), etc. In these or other embodiments, storage devices 201 can comprise (i) non-transitory memory and/or (ii) transitory memory. The one or more processors 202 can include one or more graphical processing units (CPUs), central processing units (CPUs), controllers, microprocessors, digital signal processors, and/or computational circuits. The one or more storage devices 201 can store data and instructions associated with one or more databases 210 and a neural network architecture 140 that comprises a segmentation model 230, a grading model 240, one or more loss functions 250, and a training procedure 260. The one or more processors 202 are configured to execute instructions associated with these components. Each of these components is described in further detail below.

The database 210 stores the medical images 130 that are provided to and/or analyzed by the computer vision system 150, as well as the analysis information 160 that is generated by the computer vision system 150. The database 210 also stores a set of training images 220 that are utilized to train the neural network architecture 140. Although not shown in FIG. 2, the database 10 can store any other data or information mentioned in this disclosure including, but not limited to, one or more masks (e.g., such as masks 232 and/or pseudo masks generated by the grading model), severity classification labels, one or more loss functions 250, etc.

The training images 220 can be utilized in connection with a training procedure 260 to train the segmentation model 230 and the grading model 240. The training images 220 can include various types of annotation information 225 to assist with such training. For example, the annotation information 225 can include ground-truth masks, or other related data, that includes pixel-level annotations identifying the locations of objects 135 in each of the medical images 130. The annotation information 225 can further include image-level annotations identifying severity classification labels 270 in each of the medical images 270.

Generally speaking, the severity classification labels 270 can include any label or classifier that indicates the severity or stage of a medical condition. The severity classification labels 270 can vary greatly based on the type of medical condition that is being analyzed by the computer vision system 150 and/or based on the protocols used to evaluate the medical condition. For example, for embodiments that involve diabetic retinopathy, the exemplary severity classification labels 270 may include: normal, mild, moderate, severe non-proliferative and proliferative. However, the number and types of the severity classification labels 270 for diabetic retinopathy can be varied based on different evaluation methods and protocols. Appropriate severity classification labels 270 can be designated for nearly any medical condition. For example, for embodiments that involve cancer-related medication conditions, the severity classification labels 270 may include: stage 1; stage 2; stage 3 and stage 4. Other appropriate severity classification labels 270 can be utilized for other types of medical conditions. Regardless of which medical condition is being assessed, the severity classification labels 270 can also indicate the absence of medical condition (e.g., can indicate that diabetic retinopathy conditions and/or other medical conditions were not detected in a medical image 130).

In many scenarios, the training images 220 available for training the neural network architecture 140 will only include limited pixel-level information due to the heavy, user-intensive burden associated with ascertaining such information. This is especially true in the context of medical applications. Therefore, in certain embodiments, the training images 220 can be divided into two subsets of images: a first subset of the training images that includes a relatively small number of images (e.g., 50-100 images) comprising pixel-level annotations (e.g., ground-truth masks) which identify the locations of objects 135 (e.g., lesions and/or other medical objects of interest) in the images; and a second subset of the training images that includes a relatively large number of training images (e.g., more than 10,000, 50,000 or 100,000 images) comprising only image-level annotations which identify the severity classification labels for the images. As discussed herein, specialized training procedures 260 can be utilized to train the neural network architecture 140 to accurately perform segmentation and grading functions despite the lack of pixel-wise information available for training.

The neural network architecture 140 can be trained to perform various computer vision functions. The neural network architecture 140 comprises a segmentation model 230 that is configured to execute instance or object segmentation functions 231 for identifying locations of objects 135 in the medical images 130. These functions 231 executed by the segmentation model 230 can be utilized to generate a mask 232 (also referred to a "map") for each of the medical images 130 that are analyzed. In certain embodiments, the mask 232 or map created from an image represents a binary mask or map in which the pixel values corresponding to medical objects are identified with a particular value (e.g., 1), while all other pixel values are identified with another value (e.g., 0).

The neural network architecture 140 further comprises a grading model 240 that is configured to perform classification or grading functions 241 on the medical images 130. These functions 241 executed by the grading model 240 can be utilized to determine and assign severity classification labels 270 to the medical images 130. In addition to assigning severity classification labels 270 to the images, the grading model 240 can also be configured to execute attention functions 242 that are utilized to identify locations of objects 135 in the medical images 130 and to generate pseudo masks 243 from the training images 220. Like masks 232, the pseudo masks 243 may represent binary masks that include pixel values corresponding to medical objects are identified with a particular value (e.g., 1), while all other pixel values are identified with another value (e.g., 0). The attention functions 242 generate the pseudo masks 243 by refining the masks 232 generated by the segmentation model 230 with image-level annotated data (e.g., which can be included with the second subset of training images 220). As explained in further detail below, the pseudo masks 243 can be utilized to further improve the performance of the segmentation model 230.

Figure 4:
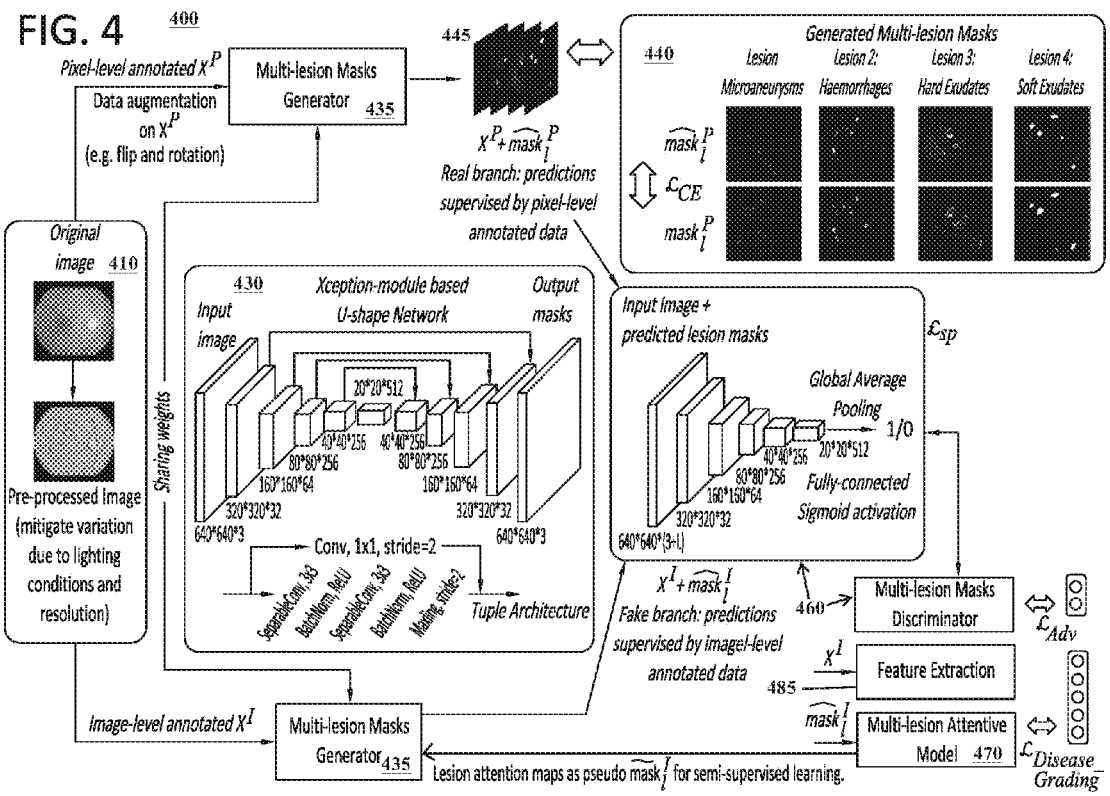
FIG. 4 is a diagram illustrating an exemplary architecture for a computer vision system in accordance with certain embodiments.

The configuration and implementation of the neural network architecture 140, including the segmentation model 130 and grading model 140, can vary. The segmentation model 130 can include one or more CNNs. In certain embodiments, the segmentation model 130 can be implemented as a U-shape neural network that includes an embedded Xception module. The U-shaped neural network can include an encoder-decoder structure that is constructed with a fully convolutional network. The Xception module is similar to an Inception module with certain adaptations being incorporated. FIG. 4, which is discussed in further detail below, provides details of an exemplary configuration for a segmentation model 130 that can be utilized to learn and execute segmentation functions 231 to identify lesions and/or other objects 135 associated with diabetic retinopathy conditions. One of ordinary skill in the art would recognize that the configuration illustrated in FIG. 4 can be easily adapted to perform segmentation functions 231 for other types of medical conditions.

Figure 5:
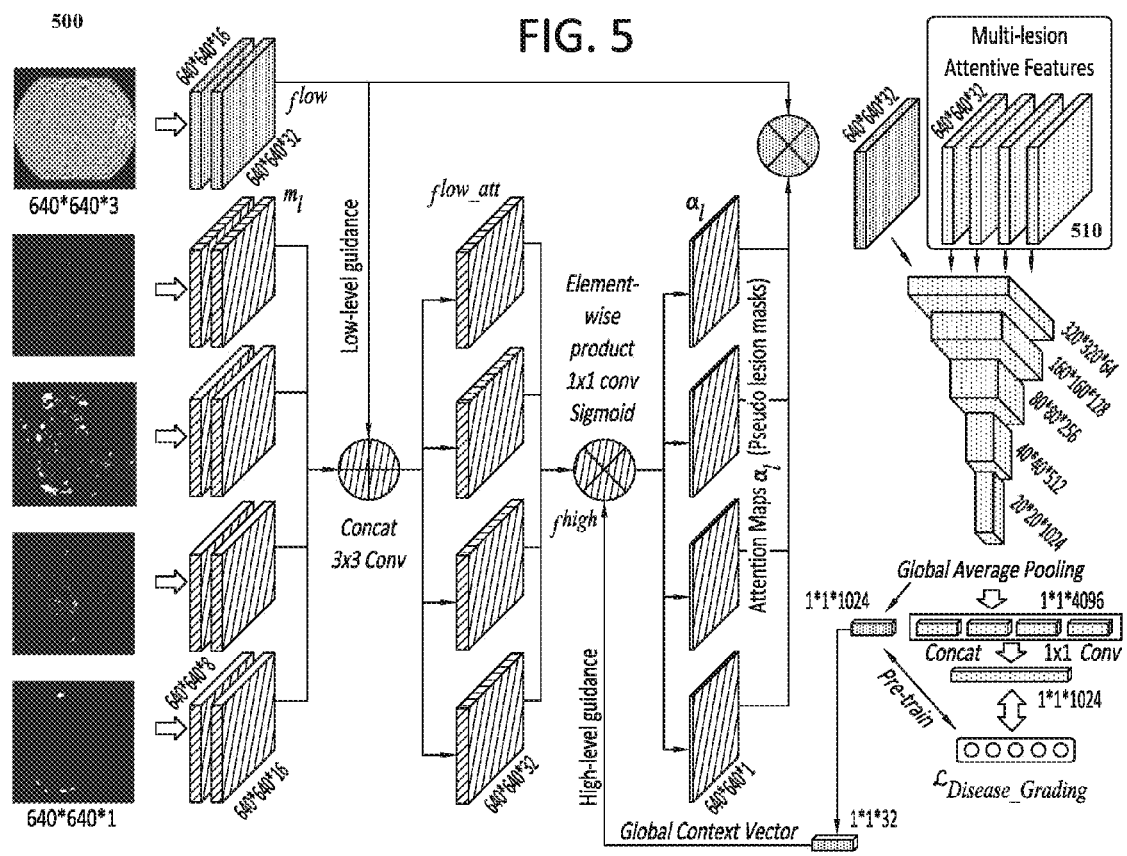
FIG. 5 is a diagram illustrating an exemplary architecture for a grading model in accordance with certain embodiments.

In certain embodiments, the grading model 240 can include a classification model that is configured to perform the grading functions 241, as well as an attention model that is configured to perform the attention functions 242. The classification model and attention model can each include a CNN, or a plurality of CNNs, that is configured to learn the grading functions 241 and the attention functions 242. FIG. 5, which is discussed in further detail below, provides details of an exemplary configuration for a grading model 140 that can be utilized to learn and execute the grading functions 241 and attention functions 242 in connection with diabetic retinopathy conditions. One of ordinary skill in the art would recognize that the configuration illustrated in FIG. 5 can be easily adapted to perform these functions for other types of medical conditions.

The training procedure 260 utilized to train the segmentation model 130 and the grading model 140 can vary. In certain embodiments, the training procedure 260 includes a semi-supervised training procedure that is based on collaborative learning approach which jointly optimizes the performance of the two models. In a first pre-training step, the segmentation model 230 can be trained using the first subset of the training images 220 (including the pixel-level annotation information 225 that includes ground-truth masks), and the grading model 240 can be trained using the second subset of the training images that include the image-level annotation information 225 (including only severity classification labels 270). In this first pre-training step, both the segmentation model 230 and the grading model 240 can be trained in a fully-supervised manner.

After the pre-training step is completed, a second training step of the training procedure 260 is executed to optimize both the segmentation model 230 and the grading model 240. At this point, the segmentation model 230 has only been trained in a weak manner given the limited training information included in the small subset of training images 220. Using this weakly-trained segmentation model 230, predicted masks (e.g., masks 232) are generated by the segmentation model 230 utilizing the segmentation functions 231 to process the second subset of training images. The weak, predicted masks are then supplied as inputs to the grading model 240 to improve the performance of the grading model 240 with respect to predicting the severity classification labels 270. These weak, predicted masks can further be utilized by the grading model 240 to generate pseudo masks 243 using the second subset of the training images 240. The pseudo masks 243 generated by the grading model can then be utilized to optimize the performance of the segmentation model 230 with respect to identifying relevant objects 135 in medical images.

Certain portions of the description below describes exemplary training procedures 260 that can be applied in the context of training the neural network architecture 240 to analyze medical images 130 associated with diabetic retinopathy conditions. One of ordinary skill in the art would recognize that these training procedures 250 can be easily adapted for other types of medical conditions.

The neural network architecture 140 can utilize one or more loss functions 250 to train and optimize the segmentation model 130 and the grading model 140. Any appropriate loss function can be utilized to train and optimize the segmentation model 130 and the grading model 140. The loss function 250 for the grading model 240 can be based on a focal loss that accounts for imbalanced data issues. The loss function 250 for the segmentation model 230 can incorporate a binary cross-entropy loss (e.g., such as $L_{CE}$ discussed below) that is used to minimize distances between the predicted masks generated during the first pre-training step of the training procedure and the ground-truths masks that are included in the annotation information 225 of the first subset of training images 220. The loss function 250 for the segmentation model 230 can further incorporate an adversarial loss (e.g., such as $L_{Adv}$ discussed below) that is optimized based on the outputs of a generative adversarial network (GAN) architecture. In contrast to traditional GAN structures which typically rely on randomly generated samples in the fake branch of the network, the pseudo masks 243 generated by the grading model 230 can be used as the samples of the fake branch and the weakly predicted masks generated by the segmentation model are used as the samples for the real branch of the network. Other types of loss functions 250 can also be utilized.

It should be apparent that the computer vision system 150 described herein can be adapted to perform automated diagnoses functions for a wide variety diseases and medical conditions, including diseases and medical conditions that are not explicitly mentioned in this disclosure. The computer vision system 150 can be adapted to perform object segmentation functions on various types of medical images 130 to detect and identify locations of various types of objects 135. Likewise, the computer vision system 150 can be adapted to analyze medial images 130 to perform grading functions associated with any medical condition of interest. The training images and procedures that enable the computer vision system 150 to learn these functions can be adapted accordingly to any medical condition of interest. Thus, while certain portions of the disclosure herein may describe embodiments that involve analysis of diabetic retinopathy, it would be apparent to one of ordinary skill in the art that such embodiments can easily be adapted to other medical conditions.

Figure 3:
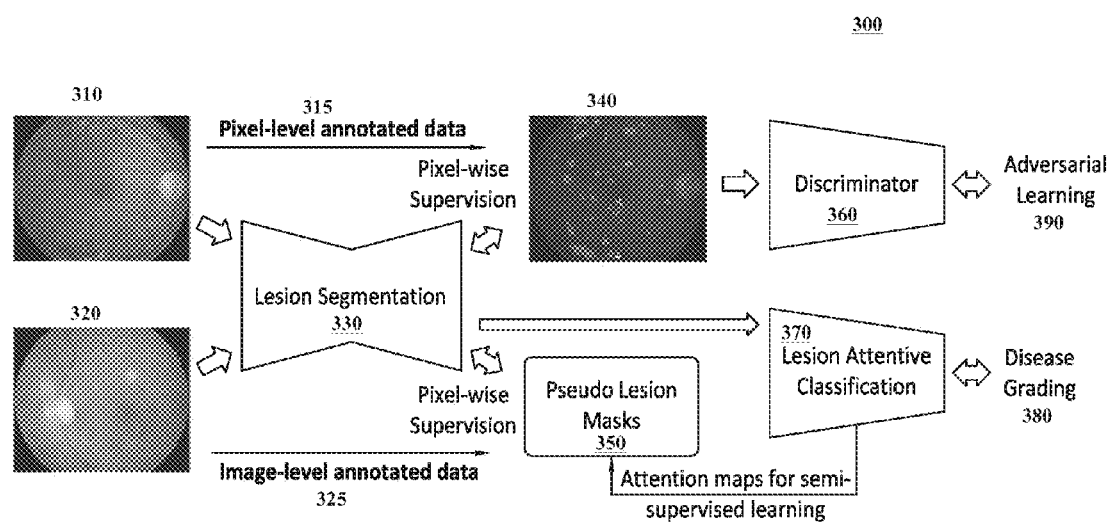
FIG. 3 is a flow diagram illustrating an exemplary collaborative learning method according to certain embodiments.

FIG. 3 illustrates a flow diagram illustrating an exemplary collaborative learning method 300 according to certain embodiments. The exemplary collaborative learning method 300 shown can be applied to learn automated diagnosis functions pertaining to diabetic retinopathy, which is an eye disease that can lead to blindness and which results from diabetes mellitus. Similar approaches can be used to learn automated diagnosis functions for other types of medical conditions.

Two sets of medical training images 220 are provided. A first subset of training images 310 has been annotated by medical experts to include pixel-level annotation information 315 (e.g., ground-truth masks) that identifies lesions objects (e.g., such as aneurysms, micro-aneurysms, hemorrhages, hard exudates, soft exudates and/or other types of lesions) in eyes that are captured in the images 310. A second subset of training images 320 has been annotated by medical experts to include image-level annotation information 325 that identifies severity classification labels 270 (e.g., lesion gradings 380) for the eyes captured in the images 320.

The training images 220 are used to train a lesion segmentation model 330 (e.g., which may correspond to segmentation model 230 in FIG. 2 in certain embodiments). To facilitate learning, the pixel-level annotation information 315 included in the first subset of training images 310 can initially be used to pre-train the lesion segmentation model 330 in a fully-supervised manner.

Then, the pre-trained lesion segmentation model 330 can process the second subset of training images 320 (which is much larger in size compared to the first subset of training images 310) to generate predicted lesion masks 340. The predicted lesion masks 340 and the second subset of training images 320 are utilized as inputs for learning a lesion attentive classification model 370. The lesion attentive classification model 370 learns to output lesion gradings 380 (e.g., severity classification labels 270) for medical images 130.

The lesion attentive classification model 370 further uses the inputs to generate pixel-level attention maps, which are then used as the pseudo masks 350 to facilitated semi-supervised learning for further refinement of the lesion segmentation model 330. More specifically, to further optimize the lesion segmentation model 330, the pseudo masks 350 and the predicted lesion masks 340 are provided as inputs to a GAN that includes a discriminator 360 for adversarial learning 390. The discriminator 360 receives the predicted lesion masks 340 in its real data branch and receives the pseudo masks 350 in its fake sample branch. The discriminator 360 attempts to distinguish the real data samples from the fake data samples, and the outputs of the discriminator 360 are utilized to further enhance the learning of the lesion segmentation model 330. The discriminator network 360 can be implemented using a convolutional network that can categorize the received images using a binomial classifier which labels each of the images as real or fake. For example, images determined to be from the real branch may be labeled 1 while images determined to be from the fake branch may be 0.

FIG. 4 is a diagram illustrating an exemplary architecture 400 for a computer vision system 150 in accordance with certain embodiments. The architecture 400 illustrates, inter alia, exemplary configurations for the neural network architecture 140 of the computer vision system 150. This figure illustrates the configuration details for the segmentation model 230, and demonstrates how it can be trained utilizing the techniques discussed in this disclosure. The bottom right portion of the figure also discloses details relating to the grading model 240, which is described in further detail below with respect to FIG. 5.

On the left side of the figure, pre-processing operations are applied to a set of training images 410 that can be utilized to train a neural network architecture of the computer vision 150 to perform automated diagnosis functions for a diabetic retinopathy condition. The training images 410 can include eye fundus images and/or other eye-related images. A first portion of the training images 410 can be annotated with pixel-level annotation information 225 (e.g., ground truth masks identifying various types of lesions in the training images 410), and a second portion of the training images 410 can be annotated with image-level annotation information 225 (e.g., severity classification labels indicating a severity of a diabetic retinopathy condition in each of the training images 410). Because the training images 410 may be captured under different lighting conditions and resolutions, the training images 410 can be pre-processed to unify the image quality and sharpen the texture details. The pre-processing functions can also include performing horizontal flips, vertical flips, and rotations on the training images 410 to augment the training dataset and to mitigate any potential imbalance of samples across different classes.

As discussed in further detail below, a multi-lesion masks generator 435 can be trained to accurately generate lesions masks 450 from medical images 130. As shown in block 440, the multi-lesion masks generator 435 can be configured to generate a plurality of lesion masks 445, each of which corresponds to a different type of lesion (e.g., micro-aneurysms, hemorrhages, hard exudates and soft exudates). Block 430 illustrates an exemplary configuration for the multi-lesion masks generator 435 and is discussed in further detail below. A multi-lesion attention model 470 is trained to determine and assign severity classification labels 270 for the images. The multi-lesion attention model 470 is also trained to generate pseudo masks that are utilized to refine the training of the multi-lesion masks generator 435.

During training, the multi-lesion masks generator 435 is initially trained in a fully-supervised manner using training images 410 which only include pixel-level annotation information 225. The weakly trained multi-lesion masks generator 435 then generates weak, predict masks 445 by processing a second set of training images that do not include pixel-level annotation information 225. As shown in block 440, a binary cross-entropy loss ($L_{CE}$) is used to minimize distances between the predictions and the ground-truth pixel-level annotation information 225. The predicted masks 445 can assist the training the multi-lesion attention model 470 to both predict severity classification labels 270 and to generate pseudo masks 243 from the training images 410. The multi-lesion attention model 470 generates the pseudo masks 243 based on features that are extracted from the second subset of training images by the feature extraction component 485 and the predicted masks 445 that are generated by the multi-lesion masks generator 435. A multi-lesion mask discriminator 460 receives the pseudo masks 243 and the predicted masks 445, and attempts to distinguish between the two. The outputs of the multi-lesion mask discriminator 460 are utilized to further refine the training of the multi-lesion masks generator 435.

Before describing further details of the architecture 400, a formulation is provided for an exemplary problem that the architecture 400 can be trained to solve. Given pixel-level annotated images $X^P$ and image-level annotated images $X^I$, one exemplary goal of the architecture 400 can be to collaboratively optimize a lesion segmentation model $G(\bullet)$ and a disease grading model $C(\bullet)$ in a manner that enables these functions to work together to improve the precision of one another. In certain embodiments, to train the segmentation model, the architecture 400 aims to minimize the difference between the predicted lesion maps and the ground-truth masks using the following function:

$$\min_G \sum_{l=1}^{L} \mathcal{L}_{Seg}(G(X^P), G(X^I), s_l^P, \tilde{s}_l^I), \qquad (1)$$

where:

$s_l^P$ denotes the ground-truth of a pixel-level annotated image P at lesion index l;

$\tilde{s}_l^I$ is a pseudo mask of image-level annotated image I at lesion index l which is learned by the lesion attentive grading model;

L is the total number of lesion varieties related to a particular disease;

G( ) denotes the lesion segmentation model;

$X^P$ are pixel-level annotated training images;

$X^I$ are image-level annotated training images; and $\mathcal{L}_{Seg}$ denotes the loss function for the lesion segmentation model.

The optimization function for the disease grading model is defined as:

$$\min L_{CIs}(C(X^I) \cdot \text{att}(G(X^I)), y^I), \qquad (2)$$

where:

att($\bullet$) indicates the lesion attention model;

$y^I$ is the disease severity classification label for image-level annotated image I;

$L_{CIs}$ denotes the objective function for the severity grading function;

$X^I$ are image-level annotated training images; and

C( ) denotes the grading model.

It should be noted that $\tilde{s}_l^I$ in Eq. 1 is equal to att($G(X^I)$). The detailed definitions of $L_{Seg}$ and $L_{CIs}$ are explained below. Therefore, to collaboratively learn the two tasks, an important factor to consider is how to design and optimize $G(\bullet)$, $C(\bullet)$ and att($\bullet$). This is discussed further below.

The exemplary network architecture 400 in FIG. 4 includes two primary portions. In a first portion, a multi-lesion masks generator 435 is proposed for learning the lesion segmentation task in a semi-supervised manner. A small-scale dataset $X^P$ is initially provided as inputs to pre-train a multi-lesion mask generator 435 in a fully-supervised manner using ground truth masks included in $X^P$. Once it is pre-trained, the large-scale dataset $X^I$ is passed through the multi-lesion mask generator 435 to generate predicted lesion maps or masks 445. A discriminator 460, optimized by an adversarial training loss, is designed to distinguish between masks generated from $X^P$ and $X^I$.

For the second part, $X^I$ and its initially predicted lesion maps 445 are adopted to learn a lesion attention model 470 (which can be included in the grading model 240 described above) that is able to determine disease grading labels (e.g., severity classification labels 270) for medical images 130. The predicted lesion maps or masks 445 are utilized by the lesion attention model 470 to generate attentive features for improving the final disease grading performance of the lesion attention model 470. Moreover, the lesion attention maps generated by the lesion attention model 470 can be used as pseudo masks to refine the multi-lesion masks generator 435 using large-scale, image-level annotation data in a semi-supervised manner. The tasks of generating lesion masks 445 and grading diseases can be jointly optimized in an end-to-end network.

Training a semantic segmentation model in this context would traditionally require large quantities of pixel-level annotated information which identifies the lesions in the training images. However, such data is not typically available for medical images because the cost of annotating the images is extremely high. Therefore, a specialized training procedure 260 can be used to train the multi-lesion masks generator 435 using limited pixel-level annotated information.

The multi-lesion mask generator 435 can be derived from a U-shape network and embedded with an Xception module for this task. The U-shape network 460 was first introduced for the segmentation of neuron structures in electron microscopic stacks. It deploys an encoder-decoder structure built with a fully convolutional network. It includes skip connections that concatenate the feature maps of contracting and expansive parts having the same spatial size. This design can best preserve the edge and texture details in the decoding process of the input images, and can also speed up the convergence time. The U-shape network can include a modified, built-in Xception module. The Xception module essentially inherits its configuration from the Inception module, with the difference being that a separable convolution performs the spatial convolution over each channel and the 1×1 convolution projects new channels independently. The Xception module is incorporated into the multi-lesion masks generator 435 for lesion segmentation because the spatial correlations over each channel of feature maps and the cross-channel correlations have less inner relationship and are not expected to jointly learn the mappings.

Block 430 of FIG. 4 illustrates a schematic diagram showing an exemplary configuration for the multi-lesion mask generator 435 of the segmentation model 230. As mentioned above, the multi-lesion mask generator 435 includes a U-shape network extended with a built-in Xception module. The U-shape network includes an encoder and decoder. Together, the encoder and decoder include a total of nine feature mapping tuples. Apart from the first tuple of the encoder, which employs normal convolution operations, the remaining tuples are designed with the Xception module. Each tuple is composed of two separable convolutions followed by batch normalization, ReLU activation, max-pooling and a shortcut of 1×1 convolution. The spatial convolution kernel size is 3×3 and the padding is set to be the same. In the decoder part, up-sampling and a skip connection are employed before each tuple. At the end, L convolution layers are added with Sigmoid activation to generate L different lesion masks. For example, as shown in block 440, different lesion masks can be provided for each of four different types of lesions. Other hyper-parameter settings can be configured appropriately.

To optimize the multi-lesion masks generator 435, both the pixel-level annotated data and the image-level annotated data can be used. With pixel-level annotated lesion masks, a binary cross-entropy loss $L_{CE}$ can be used to minimize distances between the predicted masks 445 generated by the multi-lesion masks generator 435 and the ground-truth masks included in the training images 410. Using a lesion attention model (which is discussed further below), pseudo mask ground-truths are also obtained from the image-level annotated data to optimize $L_{CE}$. Moreover, to generate better lesion masks by exploiting data without pixel-level annotations, a generative adversarial network architecture (GAN) includes a multi-lesion discriminator 460 which contributes to the training.

Traditional GANs consist of a generative net and discriminative net playing a competitive min-max game. A latent random vector z from a uniform or Gaussian distribution is usually used as the input for the generator to synthesize samples. The discriminator then aims to distinguish the real data x from the generated samples. The essential goal is to converge $p_z(z)$ to a target real data distribution $p_{data}(x)$. However, in architecture 400, rather than generating samples from random noise, the lesion maps predicted by the generator from the pixel-level annotated data is used as the real data branch and those from the image-level annotated data are used as the fake sample branch. The total loss for optimizing the lesion segmentation task can be defined as:

$$L_{Seg}=L_{Adv}+\lambda L_{CE}=\mathbb{E}\,[\log(D(X^P,G(X^P)))]+\mathbb{E}\,[\log(1-D(X^I,G(X^I)))]+\lambda\,\mathbb{E}\,[-s\cdot\log\,G(X^{(P,I)})-(1-s)\cdot\log(1-G(X^{(P,I)}))], \quad (3)$$

where:
$L_{Seg}$ denotes the loss function for the lesion segmentation model;
$L_{cls}$ denotes the objective function for the severity grading function;
λ is a weight;
$L_{Adv}$ denotes the loss function used for adversarial learning;
D denotes the descriminator;
$X^P$ are pixel-level annotated training images;
$X^I$ are image-level annotated training images;
$X^{(P,I)}$ refers to both the pixel-level annotated training images $X^P$ and image-level annotated training images $X^I$;
G( ) denotes the lesion segmentation model;
s is an expression of $s_l^P$ and $\tilde{s}_l^I$ for the ground-truths of pixel-level and image-level annotated data, respectively.

The predicted multi-lesion masks 445 are concatenated with the input images 410 and then used as inputs to the multi-lesion masks discriminator 460. The multi-lesion masks discriminator 460 has five convolution mapping tuples. Each tuple consists of two convolutional layers with kernel size of 3 and one max-pooling layer with a stride of 2 to progressively encode contextual information for an increasing receptive field. For each tuple, ReLU activation and batch normalization are also adopted. A global average pooling is employed at the end, followed by a dense connection and Sigmoid activation that provides an output (e.g., 1 or 0) indicating whether each of the received lesion masks or maps is a real mask ground-truth (e.g., which is generated by multi-lesion masks generator that was initially trained using actual pixel-level annotation data) or a pseudo mask ground-truth (e.g., which is generated using the attention model 470).

FIG. 5 is a diagram illustrating an exemplary architecture 500 for a classification or grading model 230 in accordance with certain embodiments. The grading model 230 includes two primary branches. A classification branch, which is configured to determine severity classification labels 270 for medical images, is designated in a cross-hatching pattern. An attention branch, which is configured to identify lesions and generate refined lesion masks or maps, is designed in a dotted pattern.

To grade the severity of a diabetic retinopathy condition, human experts typically determine a diagnosis by observing detailed lesion signs characteristic of the disease. While adopting a traditional deep classification model can achieve basic performance, the traditional deep classification model only has limited accuracy. Visual attention models can be configured to address recognition tasks in a human-like manner by automatically extracting task-specific regions and neglecting irrelevant information to improve their performance. Most conventional attention models are only suitable for images that include general (non-medical) objects; and are only able to predict coarse attention maps using an attention mechanism that is designed using high-level features. However, these attention models are not suitable for use with medical images in which the lesion regions are very small and are expected to be attended to in a pixel-wise manner. To address this problem, the multi-lesion attention model 470 can adopt low-level feature maps with high resolutions to guide the learning of the model 470. Moreover, for the training images that only include image-level disease grade annotations, the lesion attentive model 470 can generate pixel-level attention maps, which are then used as the pseudo masks for semi-supervised learning in the lesion segmentation model.

As shown in FIG. 5, a lesion attentive disease grading model comprises a classification branch (shown in cross-hatching) for feature extraction and classification of the input disease images, and L branches for learning the attention models of the L lesions. The lesion masks initially predicted by the segmentation model are not used to directly by the classification model because the number of pixel-level annotated medical images is usually very small, which results in the initially predicted masks being too weak to use. Moreover, the image-level grading labels can be exploited to deliver discriminative localization information to refine the lesion attention maps.

The disease grading model C( ) and lesion attention model att(•) are tightly integrated. The disease classification model can use a basic convolutional neural network in a pre-training step to learn grading functions 241 using only training images that have image-level annotation information. Once it is pre-trained, $f^{low}$ and $f^{high}$, which denote the low-level and high-level feature representations, respectively, can be extracted as pixel-wise and category-wise guidance for learning the attention model. Moreover, the initially predicted lesion maps, denoted by $m_{l=1}^L$, are encoded as inputs to the attention model. The overall expression is defined by the following equation:

$$\alpha_{l=1}^L=\mathrm{att}(f^{low},f^{high},m_{l=1}^L), \quad (4)$$

where:
$\alpha_{l=1}^L$ denote the attention maps that are output by the attention model;
att( ) denotes the lesion attention model;
$f^{low}$ denote the low-level feature representations;
$f^{high}$ denote the high-level feature representation;
$m_{l=1}^L$ denotes the lesion maps predicted by the pre-trained segementation model; and
L denotes the total number of lesions.

In the above equation, the outputs $\alpha_{l=1}^L$ are the attention maps that give high responses to different lesion regions that characterize the disease. The proposed attention mechanism can be implemented in two steps. The first step is to exploit pixel-wise lesion features by fusing the encoded low-level embeddings from both the input images and the initially predicted lesion masks. For the l-th lesion, an intermediate state can be obtained for an attentive feature by the equation:

$$f_l^{low\_att} = \text{ReLU}(W_l^{low} \text{concat}(m_l, f^{low}) + b_l^{low}), \quad (5)$$

where:

$f_l^{low\_att}$ denotes an intermediate representation of low-level attentive features;

$W_l^{low}$ denotes learnable weights on the features concatenated by predicted lesion masks and low-level features from the original images;

ReLU denotes a rectifier linear unit function;

concat( ) indicates a channel-wise concatenation;

$m_l$ denotes a lesion map predicted by the pre-trained segmentation model at index l;

$f^{low}$ denote the low-level feature representations of lesion map $m_l$; and $b_l^{low}$ denotes a learnable bias for low-level attentive features.

For the second step, a global context vector can be used to correlate the low-level attentive features and to further generate the lesion maps as:

$$\alpha_l = \text{Sigmoid}(W_l^{high}[f_l^{low\_att}|f^{high}] + b_l^{high}), \quad (6)$$

where:

$\alpha_l$ denote the attention map at index l that i output by the attention model in this step;

Sigmoid( ) denotes a Sigmoid activation function;

$\odot$ denotes an element-wise multiplication $W_l^{high}$ denotes learnable weights for the high-level attentive features;

$f_l^{low\_att}$ denotes an intermediate representation of low-level attentive features;

$f^{high}$ denote the high-level feature representation; and $b_l^{high}$ denotes a learnable bias for high-level attentive features.

The global context vector $f^{high}$ has the same channel dimension as $f_l^{low\_att}$, which is computed through a 1×1 convolution over the top layer feature from the basic pre-trained classification model. This high-level guidance includes abundant category information to weight low-level features and to refine precise lesion details. Note that $W_l^{low}$, $W_l^{high}$ bias terms are learnable parameters for the l-th lesion.

Based on the L lesion attention maps, an element-wise multiplication is conducted with the low-level image features $f^{low}$ separately and these attentive features are used to fine-tune the pre-trained disease classification model. All the lesion attentive features 510 share the same weights as the grading model and the output feature vectors are concatenated for learning a final representation. The objective function $L_{CI_s}$ for disease grading adopts a focal loss due to the imbalanced data problem. In addition, the refined multi-lesion attention maps are used as pseudo masks to co-train the segmentation model in a semi-supervised manner.

As explained above, the training scheme for the neural network architecture 140 (which can include architectures 400 and 500) can be implemented in two stages. In the first stage, the multi-lesion segmentation model can be pre-trained using the pixel-level annotated data by $L_{CE}$, and the basic disease severity classification model can be pre-trained using the image-level annotated data by $L_{CI_s}$. Both are pre-trained in a fully-supervised manner. An Adam optimizer can be adopted with the learning rate of 0.0002 and momentum of 0.5. The mini-batch size can be set to 32 for pre-training the segmentation model over 60 epochs, while the grading model is pre-trained over 30 epochs with batch size of 128.

Once the pre-training is complete, the initially predicted lesion masks generated by the segmentation model can be obtained. The predicted lesion masks can be used, along with the low-level and high-level feature representations 510 of the input images, to simultaneously train the lesion attention model for semi-supervised segmentation and to further improve the grading performance. In this stage, $L_{Adv}$ is added for semi-supervised learning and the lesion attention module is added for disease grading. The whole model is fine-tuned in an end-to-end manner. In certain embodiments, $\lambda$ in Eq. 3 can be set to 10, which has been found to yield the best performance in certain embodiments. The batch size can be set to 16 for fine-tuning over 50 epochs.

The techniques described herein can be run on a Nvidia DGX-1. Exemplary medical images 130 and/or training images 220 can be taken from the Indian Diabetic Retinopathy Image Dataset (IDRiD), EyePACS dataset and/or Messidor Dataset. Because the fundus images from different datasets have various illuminations and resolutions, a data pre-processing method can be applied to unify the image quality and sharpen the texture details. Moreover, to augment the training dataset, horizontal flips, vertical flips and rotations are conducted on the images. This can also help mitigate the imbalance of samples across different classes.

Figure 6:
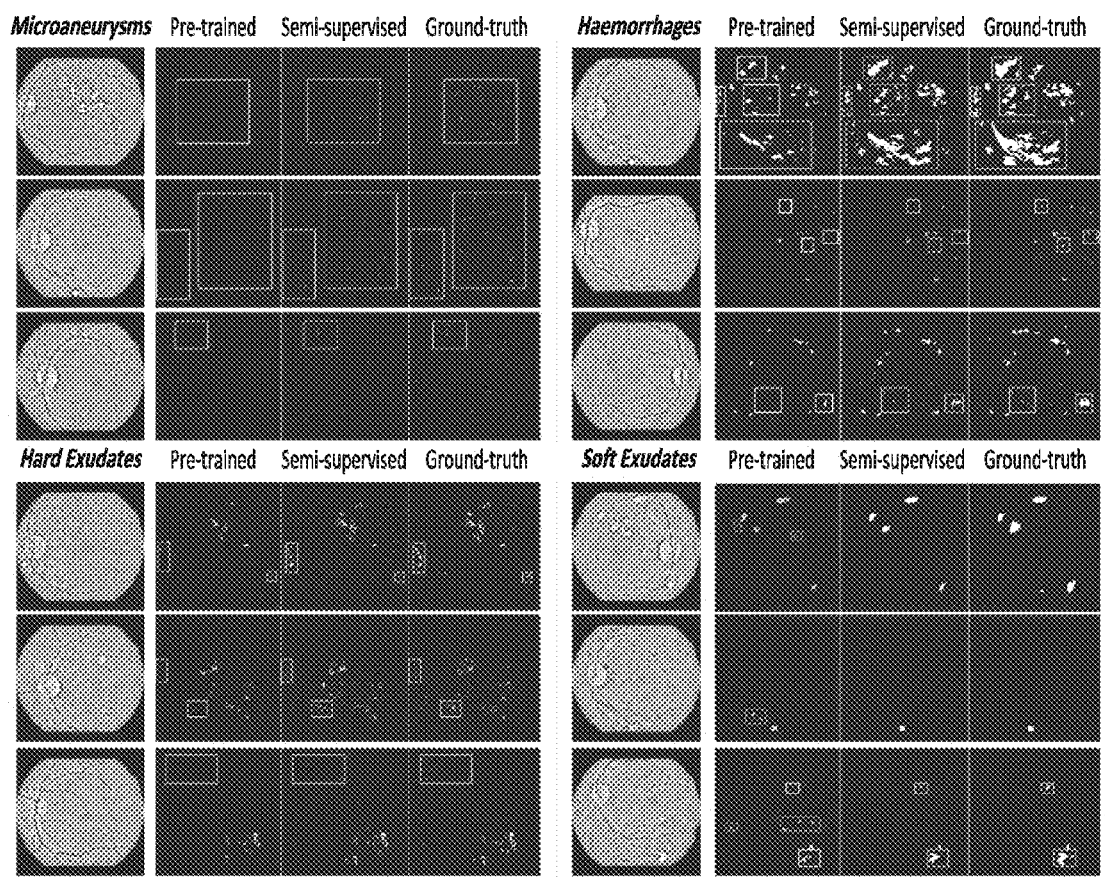
FIG. 6 is a chart showing segmentation results of exemplary experiments that were conducted according to certain embodiments.

FIG. 6 is a chart illustrating segmentation results associated with experiments that were conducting according to certain embodiments. This chart compares the segmentation results of four different lesions (i.e., micro-aneurysms, hemorrhages, hard exudates and soft exudates) for the pre-trained model, which is only trained with the limited pixel-level annotated data; and the final model, which is refined using semi-supervised training with large-scale image-level annotated data. The chart also shows ground-truth annotations that identify actual locations of the lesions in the medial images. Some or all of the images and information displayed in the chart may be output as analysis information 160 by the computer vision system 150.

Regions of the images are coarsely marked to compare the results of the pre-trained model with the final model. The green boxes denote the ground-truth annotations. The blue boxes show the results of our semi-supervised method. The yellow and red boxes highlight the miss detections and false alarms, respectively.

For the pre-trained model, the failure case usually correspondences to missed detections of the lesion patterns (i.e., false negatives). In addition, false alarms (i.e., false positives) also occur in some small regions. As can be seen, after the image-level annotated data is used to refine the segmentation model using a semi-supervised approach, the results are significantly improved over all lesions.

Figure 7:
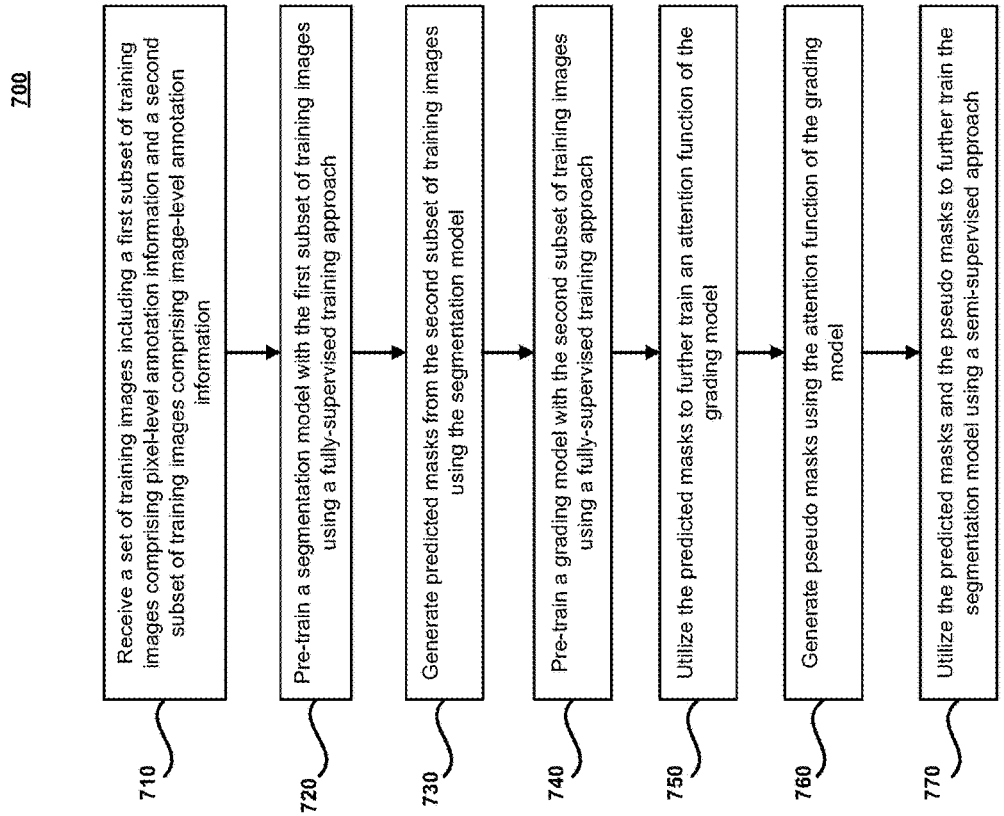
FIG. 7 is a flow chart of an exemplary method according to certain embodiments.

FIG. 7 illustrates a flow chart for an exemplary method 700 according to certain embodiments. Method 700 is merely exemplary and is not limited to the embodiments presented herein. Method 700 can be employed in many different embodiments or examples not specifically depicted or described herein. In some embodiments, the steps of method 700 can be performed in the order presented. In other embodiments, the steps of method 700 can be performed in any suitable order. In still other embodiments, one or more of the steps of method 700 can be combined or skipped. In many embodiments, computer vision system 150, neural network architecture 140, architecture 400, and/or architecture 500 can be suitable to perform method 700 and/or one or more of the steps of method 700. In these or other embodiments, one or more of the steps of method 700 can be implemented as one or more computer instructions configured to run on one or more processing modules (e.g., processor 202) and configured to be stored at one or more non-transitory memory storage modules (e.g., storage device 201). Such non-transitory memory storage modules can be part of a computer system such as computer vision system 150, neural network architecture 140, architecture 400 and/or architecture 500.

At step 710, a set of training images 220 is received which includes a first subset of training images comprising pixel-level annotation information 225 and a second subset of training images comprising image-level annotation information 225. In embodiments where a computer vision system 150 is configured to perform functions associated with diagnosing or assessing a diabetic retinopathy condition, the training images 220 can correspond to fundus images or other eye-related images. In other embodiments, the training images 220 can correspond to CT or CAT scans, x-ray scans, MRI scans, PET scans, and/or other types of medical mages. The pixel-level annotation information 225 can identify various types of medical objects (e.g., objects related to lesions or eye-related abnormalities, objects related cancer-related conditions, bone abnormalities, nerve abnormalities, heart abnormalities, etc.) based on the medical condition being analyzed by the computer vision system 150. The image-level annotation information 225 can include information that identifies one or more severity classification labels 270 associated with the medical condition being analyzed by the computer vision system 150.

At steps 720 and 730, a segmentation model 230 is pre-trained with the first subset of training images using a fully-supervised training approach and predicted masks are generated from the second subset of training images using the segmentation model. The predicted masks can represent binary masks that identify locations of medical objects in the training images with limited accuracy. During the fully-supervised training approach, a binary cross-entropy loss, or other loss, may be utilized to minimize distances between the predicted masks generated by the segmentation model and ground-truths masks that are included in the pixel-level annotation information associated with the first subset of training images. This allows for weak training of the segmentation model 230 using limited pixel-level annotation information 225.

At step 740, a grading model 240 is pre-trained with the second subset of training images using a fully-supervised training approach. Using the image-level annotations of the second subset of training images, the grading model 240 is able to learn grading functions 241 that can be used to assign severity classification labels 270 to medical images 130. After the grading model 240 is pre-trained, it is able to extract low-level and high-level feature representations from medical images 130.

At step 750, the predicted masks are utilized to further train an attention function of the grading model 240. After the grading model 240 is pre-trained, the attention function 242 of the grading model 240 can receive the predicted masks generated by the segmentation model 230, along with the low-level and high-level feature representations, as inputs. These inputs can be utilized by the grading model 240 to derive pseudo masks 243 from the images and to further improve the accuracy of the grading function 242.

At step 760, pseudo masks 243 are generated using the attention function of the grading model 240. Like the predicted masks, the pseudo masks 243 can represent binary masks that identify locations of medical objects 135 with limited accuracy.

At step 770, the predicted masks and the pseudo masks 243 are utilized to further train the segmentation model 230 using a semi-supervised training approach. As explained above, the semi-supervised training approach may utilize a GAN to refine the segmentation model. For example, the GAN may receive the predicted masks generated by the segmentation model in a real data branch and may receive the pseudo masks generated by the grading model in a fake data branch. A discriminator associated with the generative adversarial network attempts to distinguish the predicted masks from the pseudo masks; and the feedback from the discriminator is utilized to refine the segmentation model 230.

While various novel features of the invention have been shown, described and pointed out as applied to particular embodiments thereof, it should be understood that various omissions, substitutions and changes in the form and details of the systems and methods described and illustrated, may be made by those skilled in the art without departing from the spirit of the invention. Amongst other things, the steps in the methods may be carried out in different orders in many cases where such may be appropriate. Those skilled in the art will recognize, based on the above disclosure and an understanding of the teachings of the invention, that the particular hardware and devices that are part of the system described herein, and the general functionality provided by and incorporated therein, may vary in different embodiments of the invention. Accordingly, the description of system components are for illustrative purposes to facilitate a full and complete understanding and appreciation of the various aspects and functionality of particular embodiments of the invention as realized in system and method embodiments thereof. Those skilled in the art will appreciate that the invention can be practiced in other than the described embodiments, which are presented for purposes of illustration and not limitation. Variations, modifications, and other implementations of what is described herein may occur to those of ordinary skill in the art without departing from the spirit and scope of the present invention and its claims.

What is claimed is:

1. A computer vision system for analyzing medical images comprising:
one or more computing devices comprising one or more processors and one or more non-transitory storage devices for storing instructions, wherein execution of the instructions by the one or more processors causes the one or more computing devices to:
receive a set of training images including a first subset of training images comprising pixel-level annotation information and a second subset of training images comprising image-level annotation information;
execute a training procedure that jointly trains a segmentation model to identify medical objects included in medical images and a grading model to assign severity classification labels to the medical images, wherein executing the training procedure includes:
executing a pre-training procedure that uses a fully-supervised training approach to train the segmentation model with the first subset of training images and the grading model with the second subset of training images;

generating, using the segmentation model, predicted masks based on the second subset of training images after the pre-training procedure is performed;

utilizing the predicted masks to train an attention function of the grading model;

generating, using the attention function of the grading model, pseudo masks based on the second subset of training images; and utilizing the predicted masks and the pseudo masks to further train the segmentation model using a semi-supervised training approach;

receive a medical image; and generate, using the segmentation model and the grading model, analysis information for the medical image that identifies a severity classification label for the medical image and one or more medical objects included in the medical image.

2. The system of claim 1, wherein the segmentation model includes an encoder-decoder structure that is implemented, at least in part, with a fully convolutional network.

3. The system of claim 1, wherein the grading model is implemented with one or more convolutional neural networks and the grading model comprises:

a grading function that is trained to assign the severity classification labels to the medical images; and the attention function that generates the pseudo masks which are utilized to train the segmentation model using the semi-supervised training approach.

4. The system of claim 1, wherein utilizing the pseudo masks to further train the segmentation model using the semi-supervised training approach includes:

generating the pseudo masks using the attention function of the grading model;

providing the predicted masks generated by the segmentation model to a real data branch of a generative adversarial network that includes a discriminator;

providing the pseudo masks generated by the grading model to a fake data branch of a generative adversarial network;

analyzing the predicted masks and pseudo masks with the discriminator of the generative adversarial network, wherein the discriminator aims to distinguish the predicted masks from the pseudo masks; and utilizing feedback from the discriminator to further train the segmentation model.

5. The system of claim 1, wherein pre-training the segmentation model using the fully-supervised training approach includes utilizing a binary cross-entropy loss to minimize distances between the predicted masks generated by the segmentation model and ground-truths masks that are included in the pixel-level annotation information associated with the first subset of training images.

6. The system of claim 1, wherein:

the computer vision system is trained to perform functions associated with diagnosing or assessing a diabetic retinopathy condition;

the medical objects correspond to lesions objects;

the predicted masks correspond to lesion masks that identify locations of the lesion objects;

the segmentation model is trained to generate the lesion masks; and the grading model is trained to assign the severity classification label to the medical image; and the severity classification label indicates a severity or stage of the diabetic retinopathy condition associated with the medial image.

7. The system of claim 6, wherein:

the set of training images includes eye-related images;

the first subset of training images include pixel-level annotation information identifying locations of the lesion objects in the first subset of training images;

the pixel-level annotation information included with the first subset of training images includes ground-truth masks identifying the locations of the lesion objects;

the second subset of training images includes image-level annotation information that includes the severity classification labels corresponding to the diabetic retinopathy condition; and the second subset of training images is larger than the first subset of training images.

8. The system of claim 6, wherein:

the segmentation model is capable of generating the lesion masks for a plurality of lesion object types; and the plurality of lesion object types at least include: microaneurysms, hemorrhages, hard exudates, and soft exudates.

9. The system of claim 1, wherein:

the computer vision system is trained to perform functions associated with diagnosing or assessing one or more of: a cancer-related condition; a bone-related condition; a nerve-related condition; a heart-related condition; an organ-related condition; a blood-related condition; or a brain-related condition.

10. The system of claim 1, wherein the computer vision system is incorporated into, or communicates with, a system or application that provides medical services.

11. A method for providing a computer vision system that analyzes medical images comprising:

receiving a set of training images including a first subset of training images comprising pixel-level annotation information and a second subset of training images comprising image-level annotation information;

executing a training procedure that jointly trains a segmentation model to identify medical objects included in medical images and a grading model to assign severity classification labels to the medical images, wherein executing the training procedure includes:

executing a pre-training procedure that uses a fully-supervised training approach to train the segmentation model with the first subset of training images and the grading model with the second subset of training images;

generating, using the segmentation model, predicted masks based on the second subset of training images after the pre-training procedure is performed;

utilizing the predicted masks to train an attention function of the grading model;

generating, using the attention function of the grading model, pseudo masks based on the second subset of training images; and utilizing the predicted masks and the pseudo masks to further train the segmentation model using a semi-supervised training approach;

receiving a medical image; and generating, using the segmentation model and the grading model, analysis information for the medical image that identifies a severity classification label for the medical image and one or more medical objects included in the medical image.

12. The method of claim 11, wherein the segmentation model includes an encoder-decoder structure that is implemented, at least in part, with a fully convolutional network.

13. The method of claim 11, wherein the grading model is implemented with one or more convolutional neural networks and the grading model comprises:
a grading function that is trained to assign the severity classification labels to the medical images; and
the attention function that generates the pseudo masks which are utilized to train the segmentation model using the semi-supervised training approach.

14. The method of claim 11, wherein utilizing the pseudo masks to further train the segmentation model using the semi-supervised training approach includes:
generating the pseudo masks using the attention function of the grading model;
providing the predicted masks generated by the segmentation model to a real data branch of a generative adversarial network that includes a discriminator;
providing the pseudo masks generated by the grading model to a fake data branch of a generative adversarial network;
analyzing the predicted masks and pseudo masks with the discriminator of the generative adversarial network, wherein the discriminator aims to distinguish the predicted masks from the pseudo masks; and
utilizing feedback from the discriminator to further train the segmentation model.

15. The method of claim 11, wherein pre-training the segmentation model using the fully-supervised training approach includes utilizing a binary cross-entropy loss to minimize distances between the predicted masks generated by the segmentation model and ground-truths masks that are included in the pixel-level annotation information associated with the first subset of training images.

16. The method of claim 11, wherein:
the computer vision system is trained to perform functions associated with diagnosing or assessing a diabetic retinopathy condition;
the medical objects correspond to lesions objects;
the predicted masks correspond to lesion masks that identify locations of the lesion objects;
the segmentation model is trained to generate the lesion masks; and
the grading model is trained to assign the severity classification label to the medical image; and
the severity classification label indicates a severity or stage of the diabetic retinopathy condition associated with the medial image.

17. The method of claim 16, wherein:
the set of training images includes eye-related images;
the first subset of training images include pixel-level annotation information identifying locations of the lesion objects in the first subset of training images;
the pixel-level annotation information included with the first subset of training images includes ground-truth masks identifying the locations of the lesion objects;
the second subset of training images includes image-level annotation information that includes the severity classification labels corresponding to the diabetic retinopathy condition; and
the second subset of training images is larger than the first subset of training images.

18. The method of claim 16, wherein:
the segmentation model is capable of generating the lesion masks for a plurality of lesion object types; and
the plurality of lesion object types at least include: microaneurysms, hemorrhages, hard exudates, and soft exudates.

19. The method of claim 11, wherein:
the computer vision system is trained to perform functions associated with diagnosing or assessing one or more of: a cancer-related condition; a bone-related condition; a nerve-related condition; a heart-related condition; an organ-related condition; a blood-related condition; or a brain-related condition.

20. A computer program product comprising a non-transitory computer-readable medium including instructions for causing a computer to:
receive a set of training images including a first subset of training images comprising pixel-level annotation information and a second subset of training images comprising image-level annotation information;
execute a training procedure that jointly trains a segmentation model to identify medical objects included in medical images and a grading model to assign severity classification labels to the medical images, wherein executing the training procedure includes:
executing a pre-training procedure that uses a fully-supervised training approach to train the segmentation model with the first subset of training images and the grading model with the second subset of training images;
generating, using the segmentation model, predicted masks based on the second subset of training images after the pre-training procedure is performed;
utilizing the predicted masks to train an attention function of the grading model;
generating, using the attention function of the grading model, pseudo masks based on the second subset of training images; and
utilizing the predicted masks and the pseudo masks to further train the segmentation model using a semi-supervised training approach;
receive a medical image; and
generate, using the segmentation model and the grading model, analysis information for the medical image that identifies a severity classification label for the medical image and one or more medical objects included in the medical image.

* * * * *